United States Patent [19]
Yuan

[11] Patent Number: 6,153,416
[45] Date of Patent: Nov. 28, 2000

[54] IMMOBILIZATION OF MICROBIAL CELLS AND ENZYMES IN CALCIUM ALGINATE-POLYETHYLENE GLYCOL-POLYETHYLENE IMIDE BEADS

[76] Inventor: Yu-Kang Yuan, 123, University Rd., Sec. 3, Touliu, Yunlin County, Taiwan

[21] Appl. No.: 09/235,597

[22] Filed: Jan. 20, 1999

[51] Int. Cl.$^7$ .......................... C12N 11/10; C12N 11/02; C12N 11/04; C12P 1/00; C02F 3/00
[52] U.S. Cl. .......................... 435/178; 435/41; 435/177; 435/182; 435/262.5; 210/601
[58] Field of Search .......................... 435/41, 174, 177, 435/178, 180, 182, 262.5; 210/601

[56] References Cited

U.S. PATENT DOCUMENTS 4,996,150   2/1991   Joung et al. .............................. 435/161
5,175,093  12/1992   Seifert ........................................ 435/41

OTHER PUBLICATIONS

Suhaila, et al. Biotechnology Letters, vol. 4, No. 9, 1982, pp. 611–614.

*Primary Examiner*—David M. Naff
*Attorney, Agent, or Firm*—Pro-Techtor International Services

[57] ABSTRACT

Microorganisms or enzymes immobilized in beads are prepared using a combination of calcium alginate, polyethylene glycol (PEG) and polyethylene imide (PEI). An aqueous solution containing 1–14% by weight each of calcium alginate, PEG and PEI is combined with a concentrated solution of a microorganism or an enzyme to form a mixture. The mixture is combined with an aqueous solution of 4–8% w/v $CaCl_2$ to form spherical beads that are allowed to remain in the solution for 3–4 hours. Thereafter, the beads are rinsed with water for 2–3 minutes, transferred to water in a mixer, and stirred with a magnet for 6–9 hours. The resultant beads containing the microorganism or enzyme can be used for removing inorganic nitrogen and organic carbon in waste water, or in processes for making biochemical products.

9 Claims, 1 Drawing Sheet

IMMOBILIZATION OF MICROBIAL CELLS AND ENZYMES IN CALCIUM ALGINATE-POLYETHYLENE GLYCOL-POLYETHYLENE IMIDE BEADS

BACKGROUND OF THE INVENTION

The present invention relates to a process for immobilizing microorganisms, and more particularly to an immobilization process for preparing microbial beads by using calcium alginate, polyethylene glycol (PEG) and polyethylene imide (PEI).

Studies on immobilization of microorganisms confirmed the gaining of highest biomass in smallest unit volume, and the buffering and protective effects against external environmental impact. The immobilization techniques of microorganisms afford a great deal of potential of improving the wastewater treatment.

The immobilization methods of microorganisms in which various natural or synthetic polymeric substances are used to bring about the immobilization of the activated microorganisms, have received a great deal of attention in recent decades, and achieved some success in the industrial application, as exemplified by their applications in the production of biochemical products such as high fructose syrup, 6-APA, L-amino acid, etc. The immobilization methods of microorganisms include generally two types, namely, the adhesion type natural immobilization methods, and the entrapment type artificial immobilization methods. In the entrapment type artificial immobilization methods, calcium alginate is most commonly used in preparing the immobilized microbial beads. Other commonly used substances for preparing the immobilized microbial beads include polyethylene glycol (PEG), polyvinyl alcohol (PVA), K-carrageenan, aga, gelatin, etc. However, polymeric substances are toxic and expensive, and their low mechanical strength make them difficult to form beads of spherical shape. It is, therefore, important that we are in need of developing a new and inexpensive immobilization material which is not toxic to microorganisms and has a strong gel strength so as to ensure that the bead formation is successful.

PEI (polyethylene imide), PEG (polyethylene glycol and calcium alginate are non-toxic to microorganisms. When mixed well, the mixture of PEI, PEG and calcium alginate has advantages that it is non-toxic to both human being and microorganisms, and that it is provided with a mechanical strength sufficiently strong enough to ensure the success of bead formations, and further it can be used in industry and produced in quantity economically. Therefore, the mixture of PEI, PEG and calcium alginate is an ideal material for use in immobilizing microorganisms.

Various patented methods of immobilizing microorganisms by PVA have been disclosed in recent years, as exemplified by the exemplified by the Japanese patent applications Kokai 57-14129 (1982) and 61-139385 (1986) in which the entrapment methods are characterized that the gelations of the mixture containing the PVA aqueous solution and the microorganisms are carried out by the methods associated with the freezing and thawing technique. Another Japanese patent application Kokai 1-454372 (1989) discloses a method, in which the mixture of the PVA aqueous solution and the microorganisms is exposed to the ultraviolet radiation so as to form a photocrosslinking gelation. Another gelation technique is shown in U.S. Pat. No. 5,290,693, in which PVA, boric acid and phosphate are used for immobilizing microorganisms.

The prior art described above have the following shortcomings. In the first place, they are time-consuming and complicated, thereby resulting in a substantial increase in the expenditure for large-scale production facilities without increasing the productivity. Secondly, an environment in which cryogenic temperature, vacuum and boric acid are present is antagonistic to the living microorganisms intended to be immobilized. In the third place, their high density structure affect the delivery of gas and substances, thereby causing the gelations not suitable for a long term use.

SUMMARY OF THE INVENTION

It is, therefore, the primary objective of the present invention to provide a simple, low-cost energy-saving and timesaving process for preparing immobilized microbial beads for application in waste water treatment and biochemical industry. It is another object of the present invention to provide a process for preparing immobilized microbial beads, in which the mixture of 3 ml high concentration of microorganisms or enzymes and 100 ml calcium alginate-PEG-PEI solution is treated for gelation in a 4–8 weight % $CaCl_2$ fixation solution. Microbial beads are immobilized in fixation solution for a period of 3–4 hours, then washed with clean water for 2–3 minutes, and then put in clean waster, and mixed by magnetic stones for a period of 6–9 hours, for enabling PEG to be released in solution. The mixture is then preserved in a refrigerator under 4° C. for further use. Such method can be carried out easily without subjecting the microorganisms to toxic substances.

The present invention uses high molecular material (calcium alginate, PEG) to form with positive charge carried, high molecular electrolysis of PEI a net structure. The net structure is reinforced through an exchange with calcium ions, enabling the water-proving property and mechanical strength of the microbial beads to be greatly improved. The immobilization of bridge coupling of microorganisms or enzymes in the net structure is not only harmless to the microorganisms but also favorable for vitalizing the microorganisms.

DETAILED DESCRIPTION OF THE PREFERRED EMBODIMENT

Figure 1:
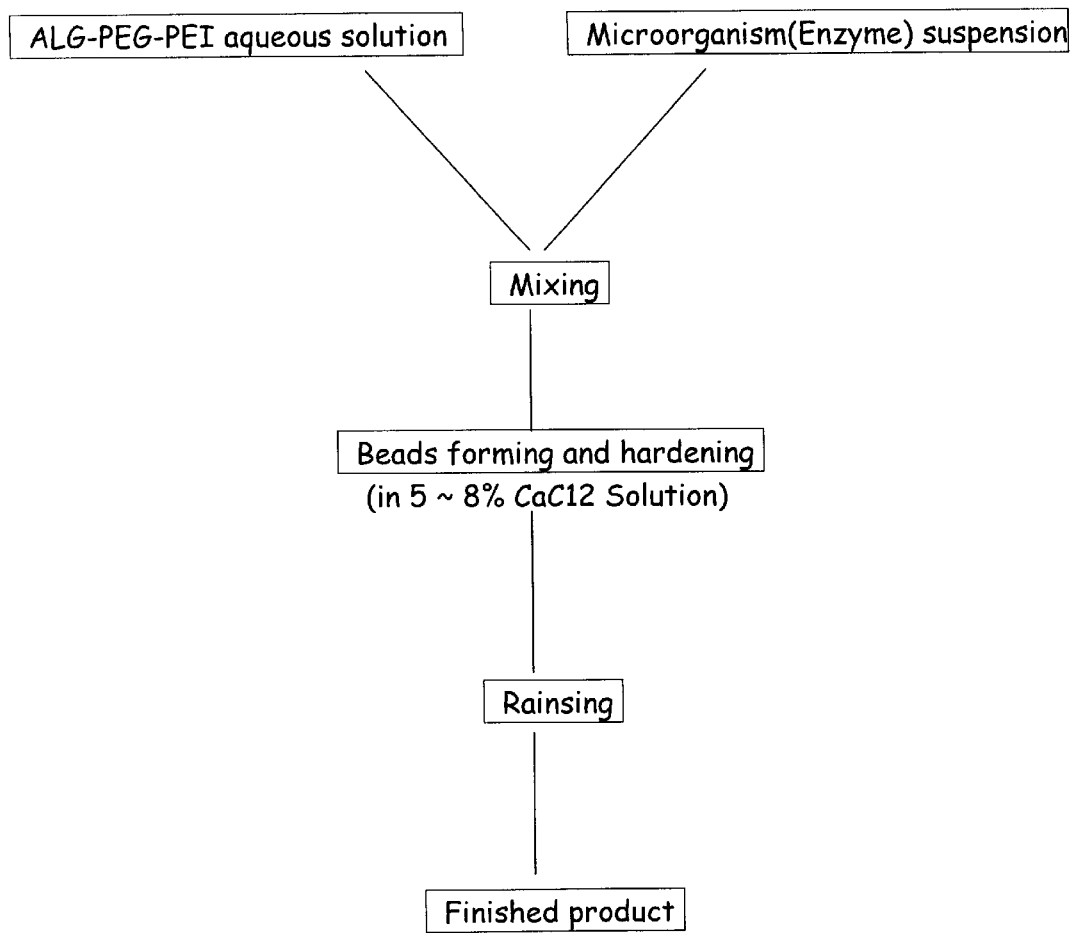
FIG. 1 is an immobilized microbial beads preparation flow chart according to the present invention.

The method of the present invention uses calcium alginate 1–14 wt %, PEG (polyethylene glycol) 1–14 weight %, and PEI (polyethylene imide) 1–14 weight %. Calcium alginate is a natural polyose, whose +2 ions cause the solution to be gelled. PEI is a positive electricity-carried high polymer that attracts Alg electrically, causing the structure of the beads to be reinforced. PEG is a hydrophilic substance used to wash the beads, making the beads transparent. The PEG has an average molecular weight of about 1900–2000, and the PEI has an average molecular weight of about 70,000.

The present invention is characterized in that the fundamental framework of gelation is permitted to establish in a calcium chloride solution for a limited period of time. As a result, the likelihood that the calcium chloride does some damage to the microorganisms or the enzymes is reduced to a minimum.

The immobilization process of the present invention can be used effectively to immobilize enzymes, industrial microorganisms, waste water treatment microorganisms, animal and plant cells, etc. Some of the enzymes that can be immobilized by the immobilization process of the present invention are fermentation yeasts, nitric bacteria, denitration bacteria, activated sludge microorganism, anaerobic sludge microorganisms, methanogens, denitrifying sludge microorganisms, etc.

EXAMPLE I

An aqueous solution (100 ml) containing 14% by weight of calcium alginate+PEG+PEI was mixed thoroughly with a concentrated solution (3 ml) of microorganisms. This mixture was then added with 4–8%(w/v)$CaCl_2$ (specific gravity about 1.01–1.05, mechanical strength about 41.4–48.8%) drop by drop to form spherical beads having a diameter on the order of 3–3.6 mm, Such spherical beads were allowed to remain in the aqueous solution for 3–4 hours. Thereafter, these beads were rinsed with water for 2–3 minutes, and then transferred to clean water in a mixer and then stirred up with a magnet for 6–9 hours. The 135 g of these immobilized microbial beads were mixed with 500 ml waste water containing nitrogen 154 mg/l, COD 210 mg/l. This mixture was kept in a 1000 ml beaker. After being cultivated for 7 days, the diameter of the immobilized microbial beads was reduced to 2.4–2.8 mm, specific gravity reduced to 1.02–1.09, mechanical strength was changed to 33.5–61.2, the concentration of nitrogen and COD were reduced to 0.2 mg/l and 7.8 mg/l respectively.

EXAMPLE II

An aqueous solution (100 ml) containing 14% by weight of calcium alginate+PEG+PEI was mixed thoroughly with a concentrated solution (4 ml) of microorganisms. This mixture was then added with 4–8%(w/v)$CaCl_2$ (specific gravity about 1.01–1.05, mechanical strength about 41.4–48.8%) drop by drop to form spherical beads having a diameter on the order of 3–3.6 mm. Such spherical beads were allowed to remain in the aqueous solution for 3–4 hours. Thereafter, these beads were rinsed with water for 2–3 minutes, and then transferred to clean water in a mixer and then stirred up with a magnet for 6–9 hours. The 128 g of the immobilized microbial beads thus obtained were exposed to 0.2% (w/v) nutrient broth for 5 hours, then 12 g of the immobilized microbial beads were taken out and transferred to a BOD bottle having a capacity of 300 ml. The microbial beads loading rate in the BOD bottle was 4%. The BOD bottle was then filled up with the saturated nutrient broth. A calibrated SVNTEX D.0 meter, SD-70 was inserted into the BOD bottle, which was stirred up with Fargo MS-90 (the speed of Fargo MS-90 was adjusted to 4). Recording was started when oxygen dissolving rate became stable. At the 96th hour, the oxygen absorbing rate of the immobilized microbial beads was 45.4–49.8 mgO2/hr. This result indicates high activity of the immobilized microbial beads.

EXAMPLE III

An aqueous solution (100 ml)) containing 14% by weight of calcium alginate+PEG+PEI was mixed thoroughly with a concentrated solution (6 ml) of microorganisms. This mixture was then added with 4–8%(w/v)$CaCl_2$ drop by drop to form spherical beads having a diameter on the order of 3–3.6 mm (specific gravity 1.01–1.05, mechanical strength 41.4–48.8%). Such spherical beads were allowed to remain in the aqueous solution for 3–4 hours. Thereafter, these beads were rinsed with water for 2–3 minutes, and then transferred to water in a mixer and then stirred up with a magnet for 6–9 hours. 100 pieces of the beads were taken from a total of 130 g immobilized microbial beads thus obtained, and evenly transferred to four flasks having a capacity of 100 ml, which flasks were respectively filled with 80 ml living waste water. The waste water in each flask was stirred up, and replaced once per every 24 hours, and the suspended number of beads was simultaneously recorded upon replacement of waste water. 15 days after test, the suspended number of beads was below 1%. This result indicates an excellent conversion rate of the beads.

EXAMPLE IV

An aqueous solution (100 ml) containing 14% by weight of calcium alginate+PEG+PEI was mixed thoroughly with a concentrated solution (5 ml) of microorganisms. This mixture was then added with 4–8%(w/v)$CaCl_2$ drop by drop to form spherical beads having a diameter on the order of 3–3.6 mm (specific gravity 1.01–1.05, mechanical strength 41.4–48.8%). Such spherical beads were allowed to remain in the aqueous solution for 3–4 hours. Thereafter, these beads were rinsed with water for 2–3 minutes, and then transferred to water in a mixer, and stirred up with a magnet for 6–9 hours, to form 125 g immobilized microbial beads. 4 g of the immobilized microbial beads was taken out and divided into 12 groups, and then respectively put in (0.1%, 0.5%, 1.0%) $MnSO_4$, $H_2O$, (0.1%, 0.5%, 1.0%) $CuSO_4$, $H_2O$, (0.1%, 0.5%, 1.0%) $Al_2(SO_4)_3$, $14H_2O$ and (0.1%, 0.5%, 1.0%)$FeCl_3$, $6H_2O$ solutions for 3 days, and then the mechanical strength was measured. The result showed the ion concentration increased, the effect of $Cu^{+2}$ reduced, i.e., the mechanical strength of the immobilized microbial beads was reduced while the concentration of copper ions increased.

EXAMPLE V

An aqueous solution (100 ml)) containing 14% by weight of calcium alginate+PEG+PEI was mixed thoroughly with a concentrated solution (100 ml) of microorganisms. This mixture was then added with 4–8%(w/v)$CaCl_2$ drop by drop to form spherical beads having a diameter on the order of 3–3.6 mm (specific gravity 1.01–1.05, mechanical strength 41.4–48.8%). Such spherical beads were allowed to remain in the aqueous solution for 3–4 hours. Thereafter, these beads were rinsed with water for 2–3 minutes, and then transferred to water in a mixer, and stirred up with a magnet for 6–9 hours, to form 1270 g immobilized microbial beads. 7 flasks having a capacity of 1000 ml were taken, and respectively added with 0, 50, 100, 150, 200, 250, and 300 g of the immobilized microbial beads, and then respectively filled with 1000 ml fresh living waste water, enabling the loading rate of immobilized microbial beads in the flasks to be 0%, 5%, 10%, 15%, 20%, 25% and 30%. These flasks were stirred up at 100 rpm, and equally exposed to aeration at 498 cm3Air/min. After 3, 6, 9, 12 hours, stirring and aeration actions were stopped, and the values of COD, $NH_3$—N, $NO_3$—N were measured. When at 9th hour, the COD removal rate in 10~30% immobilized microbial beads loading rate was approximately at 80%, preferably 81.6% (removal rate) in 15% (loading rate), or 82.6% (removable rate in 20% (loading rate). The best $NH_3$—N removal rate reached 95.5% in 25% loading rate when at the 12th hour. The best $NO_3$—N removal rate reached 97.8% in 15% loading rate when at the 12th hour.

EXAMPLE VI

An aqueous solution (100 ml)) containing 14% by weight of calcium alginate+PEG+PEI was mixed thoroughly with a concentrated solution (6 ml) of microorganisms. This mixture was then added with 4–8%(w/v)$CaCl_2$ drop by drop to form spherical beads having a diameter on the order of 3–3.6 mm (specific gravity 1.01–1.05, mechanical strength 41.4–48.8%). Such spherical beads were allowed to remain in the aqueous solution for 3–4 hours. Thereafter, these beads were rinsed with water for 2–3 minutes, and then transferred to water in a mixer, and stirred up with a magnet for 6–9 hours, to form 128 g immobilized microbial beads. An UAFBR (upflow aeration fluidized bed reactor) was used and filled with the immobilized microbial beads at a loading rate of 15%. Hydraulic power remained for 9 hours. Synchronous comparison was made with waste water treatment plant of National Yung-Lin Technology University, Taiwan (using extended aeration sludge activating method, hydraulic power remaining time about 22 hours). Experimentation lasted for 60 days. The result shows that the average COD removal rate of the waste water treatment plant is 90.3%, $NH_3$—N average removal rate is 96.1%, and an accumulation of $NO_3$—N is observed; the average COD removal rate of the immobilized microbial beads in UAFBAR is 81.4%, $NH_3$—N average removal rate is 91.4%, and accumulation of $NO_3$—N is 50 mg/l less in comparison with the waste water treatment plant. This result indicates that the immobilized microbial beads are effective in removing inorganic nitrogen under an aerobic environment. After a continuous 60-days operation, the immobilized microbial beads still remain intact, springy, and not fragile.

What the invention claimed is:

1. A process for preparing microbial cells or enzymes immobilized in beads, said process comprising the steps of:
   i) preparing an aqueous solution by mixing 1–14 weight percent calcium alginate, 1–14 weight percent polyethylene glycol and 1–14 weight percent polyethylene imide with water;
   ii) mixing the aqueous solution from step i) with 6 ml of a concentrated solution of a microorganism or an enzyme to form a mixture;
   iii) subjecting the mixture to a gelation treatment and hardening treatment by contacting the mixture with 4–8% w/v $CaCl_2$ for 3–4 hours to form spherical beads; and
   iv) rinsing the spherical beads with water for about 2–3 minutes, and then transferring the spherical beads to water in a mixer and mixing for 6–9 hours to obtain said microbial cells or enzymes immobilized in beads.

2. The process of claim 1 wherein said polyethylene glycol has an average molecular weight of about 1900–2000, and said polyethylene imide has an average molecular weight of about 70,000.

3. The process of claim 1 wherein the concentration of $CaCl_2$ in step iii) is about 4 w/v %.

4. The process of claim 1 wherein said gelation treatment and said hardening treatment proceed simultaneously for 3–4 hours.

5. The process of claim 1, wherein said 6 ml concentrated solution of a microorganism or an enzyme is prepared by culturing a microorganism in a culture medium and then concentrating the medium by a centrifugal process.

6. The process of claim 1 wherein said microorganism is bacteria, fungi, algae, or protozoda.

7. The process of claim 1 wherein said microorganism is an acclimatized activated sludge microorganism in living waste water.

8. The process of claim 1 wherein said microorganism is an acclimatized activated sludge microorganism in agricultural or industrial waste water.

9. The process of claim 1 wherein said enzyme is amylase, cellulase, or proteinase.

* * * * *